United States Patent [19]

McEntee et al.

[11] 4,220,609
[45] Sep. 2, 1980

[54] PROCESS FOR THE RECOVERY OF ALKYL CHLORIDES

[75] Inventors: Harry R. McEntee, Waterford; Frank S. Potochnik, Scotia, both of N.Y.

[73] Assignee: General Electric Company, Waterford, N.Y.

[21] Appl. No.: 748,740

[22] Filed: Dec. 9, 1976

Related U.S. Application Data

[60] Division of Ser. No. 641,655, Dec. 17, 1975, Pat. No. 4,025,352, which is a continuation-in-part of Ser. No. 359,842, May 14, 1973, abandoned.

[51] Int. Cl.² ............................................. C07C 17/00
[52] U.S. Cl. ................................ 260/657; 260/652 R; 423/481
[58] Field of Search ........................... 260/657, 652 P; 423/488

[56] References Cited

U.S. PATENT DOCUMENTS

| | | | |
|---|---|---|---|
| 2,047,611 | 7/1936 | Baxter | 423/488 |
| 2,091,986 | 9/1937 | Holt et al. | 260/657 |
| 2,244,629 | 6/1941 | Livak et al. | 260/657 |
| 2,421,441 | 6/1947 | Thronson et al. | 260/652 |
| 2,516,638 | 7/1950 | McCurdy | 260/657 |
| 2,622,107 | 12/1952 | Mattson | 260/657 |

FOREIGN PATENT DOCUMENTS

| | | | |
|---|---|---|---|
| 691295 | 7/1964 | Canada | 260/657 |
| 2422969 | 12/1974 | Fed. Rep. of Germany | 260/657 |

Primary Examiner—Delbert E. Gantz
Assistant Examiner—Joseph A. Boska
Attorney, Agent, or Firm—Morgan, Finnegan, Pine, Foley & Lee

[57] ABSTRACT

Crude gaseous $C_1$-$C_3$ alkyl chlorides, prepared by reacting the corresponding alcohol with hydrogen chloride, are freed from by-product water, unreacted hydrogen chloride and unreacted alcohol by feeding the superheated gaseous stream to an acid removal distillation unit with steam wherein the hydrogen chloride is removed as an acid by-product stream; thereafter passing the alkyl chloride vapors into a refrigerated recovery distillation unit wherein the alcohol is liquified; and finally withdrawing and recovering the $C_1$-$C_3$ alkyl chloride from the refrigerated recovery distillation unit. In an embodiment, the process includes passing the alkyl chloride vapors from the acid removal distillation unit into an aqueous caustic scrubbing unit and withdrawing the spent caustic and recycling it to the acid removal distillation unit, prior to passing the alkyl chloride vapors to the refrigerated recovery distillation unit.

18 Claims, 2 Drawing Figures

PROCESS FOR THE RECOVERY OF ALKYL CHLORIDES

CROSS-REFERENCE TO RELATED APPLICATION

This is a division of application Ser. No. 641,655, filed Dec. 17, 1975, now U.S. Pat. No. 4,025,352, which is a continuation-in-part of Ser. No. 359,842, filed May 14, 1973, now abandoned.

This invention relates to a process for the preparation of chlorinated organic compounds. It is concerned with an improved process for production of alkyl halides by reacting the corresponding alcohol with hydrogen chloride. In particular, the invention concerns a novel process sequence for treating crude alkyl chloride product streams, the sequence comprising acid removal distillation and refrigerated alcohol recovery distillation, following which the alkyl chlorides are recovered in substantially pure and dry form.

BACKGROUND OF THE INVENTION

In E. A. Thronson et al, U.S. Pat. No. 2,421,441, there is described a process for the production of methyl chloride by reacting methanol with hydrogen chloride. A crude gaseous product is obtained which, besides methyl chloride, also contains unreacted hydrochloric acid, unreacted methanol, water and dimethyl ether. Removal of the by-products and reactants was accomplished according to the U.S. Pat. No. 2,421,441 by scrubbing the gaseous stream sequentially with water, with dilute sodium hydroxide solution, and with concentrated sulfuric acid. Operation of such a process has tended to be economically expensive as well as subject to a severe environmental problem because large volumes of water are required for the absorption and distillation vessels and the water scrubber effluent is loaded with organics, principally methanol, when it is sent to waste disposal facilities. In J. L. McCurdy, U.S. Pat. No. 2,516,638, another approach is suggested for the production of ethyl chloride, n-propyl chloride and i-propyl chloride from the corresponding alcohols. In the U.S. Pat. No. 2,516,638 the reaction is carried out in the presence of an azeotrope-forming liquid, which is used to help separate the alkyl halide from the alcohol after cooling in a decanter and removing the layers which form. Although the process of the U.S. Pat. No. 2,516,638 contemplates recycle of the unreacted alcohol back into the production reactor, the need to add the azeotrope-forming liquid is disadvantageous because of the expense and for the further reason that some of them, e.g. carbon tetrachloride, are toxic, and others, e.g., benzene are highly flammable. In G. W. Mattsen, U.S. Pat. No. 2,622,107, the vaporized alkyl chloride mixture with unreacted alcohol and by-product HCl is fed first to a refrigerated cooler, then to a compressor and caustic scrubber.

To summarize the disadvantages in the processes represented by present state of the art: (i) they require the discharge of organics, principally the alcohol, to the plant effluent stream, as the alkyl chloride is purified; (ii) the cost of removing alcohol and other organics from the plant waste stream is high; (iii) it is difficult to dispose of spent caustic solutions containing unreacted alcohols; (iv) large volumes of steam and water are required in the absorption and distillation processes to recover alcohols from plant waste streams in purities adequate for re-use in the product reactor; and (v) large volumes of water are also needed to scrub the alcohols out of the gaseous alkyl chloride stream.

There has now been discovered a novel process which combines in the sequence stated, an acid removal distillation with steam and then a refrigerated, alcohol recovery distillation. This process removes all of the above enumerated disadvantages of the present alkyl chloride manufacturing process and efficiently avoids pollution of environmental waters by removing organics before they can be discharged in plant effluent streams. If the acid content is high, a caustic scrubbing step intermediate the acid removal distillation step and the refrigerated recovery step is very advantageous.

To summarize the advantages of the present process: (i) the alcohol remaining in the product of the alkyl halide reactor is recovered in a purity sufficient for recycle to the production reactor; (ii) discharge of organics to the plant waste stream is reduced to very low levels, in compliance with environmental quality standards; (iii) if used, the caustic scrubber effluent is stripped free of organics, instead of being discharged directly to the plant waste stream; (iv) direct distillation uses the superheated vapor feed and relatively minor amounts of steam thereby reducing heat loads and saving in the costs and investment for providing steam and water; (v) the by-product hydrochloric acid solution discharged from the process is low in organics and thus may be used for alkali neutralization and other plant processes; and (vi) in another embodiment, refrigeration for the recovery distillation is provided economically by recycle of methyl chloride from the product compressor.

DESCRIPTION OF THE DRAWINGS

The drawings are diagramatic representation in flowsheet form of apparatus for carrying out the method of the invention, in which.

DESCRIPTION OF THE INVENTION

Figure 1:
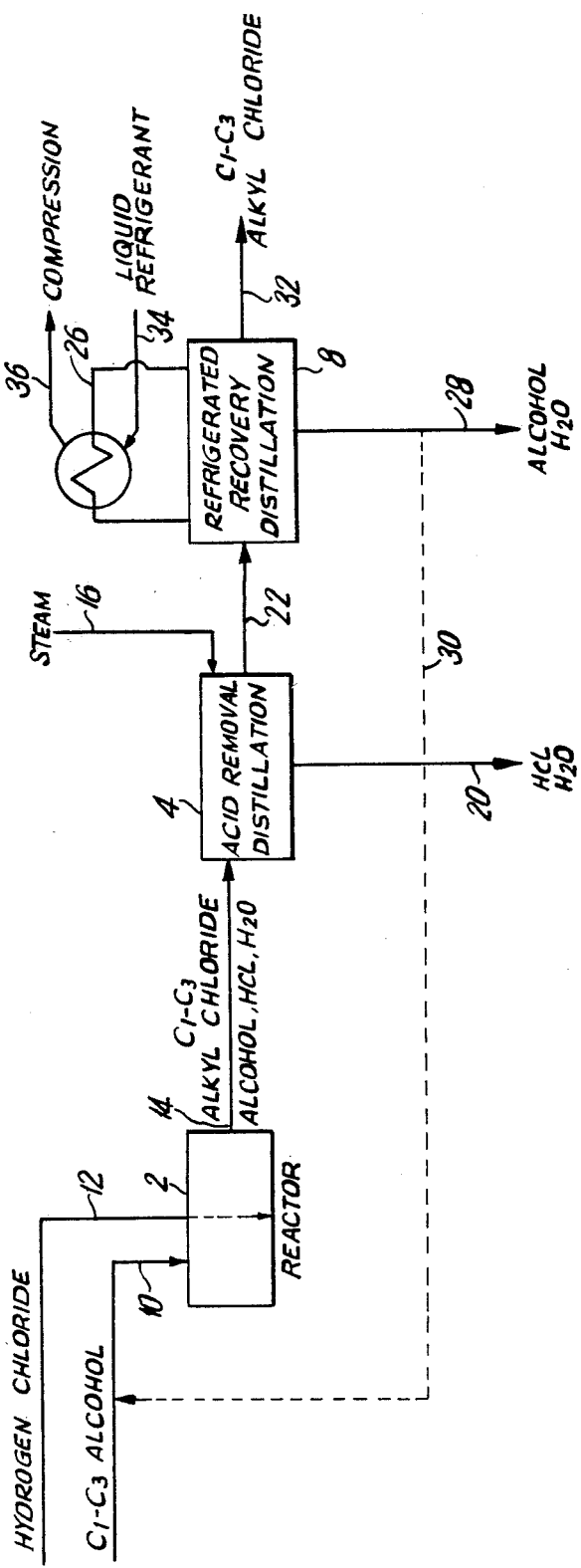
FIG. 1 shows the process wherein the alkyl chloride vapors are sent directly from the acid removal distillation vessel to the refrigerated recovery unit.

According to the present invention, there is provided in a process for the preparation of a $C_1$–$C_3$ alkyl chloride by reacting a $C_1$–$C_3$ alcohol and hydrogen chloride in a production reactor to produce a superheated vapor of the $C_1$–$C_3$ alkyl chloride by-product water, unreacted hydrogen chloride and unreacted $C_1$–$C_3$ alcohol, an improvement which comprises:

(a) feeding said superheated vapor and steam to an acid removal distillation vessel to produce an acid by-product solution of substantially all of the hydrogen chloride and removing the acid by-product solution from the vessel;

(b) withdrawing the gaseous $C_1$–$C_3$ alkyl chloride from the acid removal distillation vessel and passing it into a refrigerated recovery distillation vessel wherein the unreacted $C_1$–$C_3$ alcohol is liquified and removing the liquified $C_1$–$C_3$ alcohol from the vessel; and (c) withdrawing and recovering the gaseous $C_1$–$C_3$ alkyl chloride from the refrigerated recovery distillation vessel.

If the hydrochloric acid content is relatively high, the process is modified by using an improvement which comprises:

(a) feeding the superheated vapor and a spent aqueous caustic recycle solution to an acid removal distillation vessel to produce an acid-by-product solution of the major proportion of the hydrogen chloride and removing the acid-by-product solution from the vessel;

(b) withdrawing the gaseous $C_1$-$C_3$ alkyl chloride from the acid removal distillation vessel and passing it into a scrubbing vessel, intimately contacting it therein with an aqueous caustic solution to remove the remaining proportion of the hydrogen chloride and to produce an alcohol-containing spent aqueous caustic recycle solution and recycling said solution from the scrubbing vessel to the acid removal distillation vessel in step (a);

(c) withdrawing the gaseous $C_1$-$C_3$ alkyl chloride from the scrubbing vessel and passing it into a refrigerated recovery distillation vessel wherein the unreacted $C_1$-$C_3$ alcohol is liquified and removing the liquified $C_1$-$C_3$ alcohol from the vessel; and (d) withdrawing and recovering the gaseous $C_1$-$C_3$ alkyl chloride from the refrigerated recovery distillation vessel.

In a preferred aspect, the liquified, unreacted $C_1$-$C_3$ alcohol recovered from the refrigerated vessel of step (c) is recycled into the $C_1$-$C_3$ alkyl chloride production reactor. In another preferred feature, the refrigerant in the recovery distillation vessel is methyl chloride.

As is the case of U.S. Pat. No. 2,421,441, the alkyl chloride produced can be methyl chloride or, as in the case of U.S. Pat. No. 2,516,638, the feed for the process can be a crude gaseous stream of ethyl chloride, n-propyl chloride or i-propyl chloride, the corresponding alcohols being methanol, ethanol, n-propanol and i-propanol. In all cases, because of its wide applicability as a chemical intermediate and because it serves usefully as a refrigerant in the process, the process is especially adaptable to the preparation of methyl chloride.

In the present invention, the $C_1$-$C_3$ alkyl chloride is formed, along with small amounts of the corresponding $C_1$-$C_3$ dialkyl ether, by reacting the corresponding $C_1$-$C_3$ alcohol with hydrochloric acid in the presence of a conventional catalyst, for example, zinc chloride. A crude gaseous product is obtained in this manner, which contains unreacted hydrogen chloride, unreacted $C_1$-$C_3$ alcohol and by-product water, as well as the product and the corresponding ether.

The process in its broadest aspects is most readily understood by reference to FIG. 1. The gas, which usually leaves production reactor 2 at a superheated state, e.g., 130°-150° C., is fed to suitable vessel 4, e.g., a packed column, in which the hydrogen chloride is removed by selective extraction-condensation as an aqueous stream with results from the condensation by steam which is also fed to the vessel. The hydrogen chloride forms a solution of, e.g., 5-20% concentration and is discharged from the process through conduit 20 at this point. It is low in by-product organics and is suitable for further use, e.g., in alkali neutralization or other plant processes.

Next, the vapors of alkyl chloride from which substantially all of the hydrogen chloride has been removed in acid removal distillation vessel 4 are sent to refrigerated vessel 8 of any conventional design and the unreacted $C_1$-$C_3$ alcohol is liquified and removed from the stream. Any conventional refrigerant can be used, but methyl chloride is preferred because it is economical and efficient. The liquid alcohol (together with some alkyl chloride and water) which is withdrawn from vessel 8 can be stored and re-used. However, it is surprisingly pure enough to permit its recycling to the production reactor, as is, for re-use in the process.

Finally, the gaseous $C_1$-$C_3$ alkyl chloride from the preceeding step is withdrawn from the process through conduit 34 and recovered. Any conventional means for recovery can be used, but it is convenient to make a final drying and then to liquify it, e.g., by compression.

Figure 2:
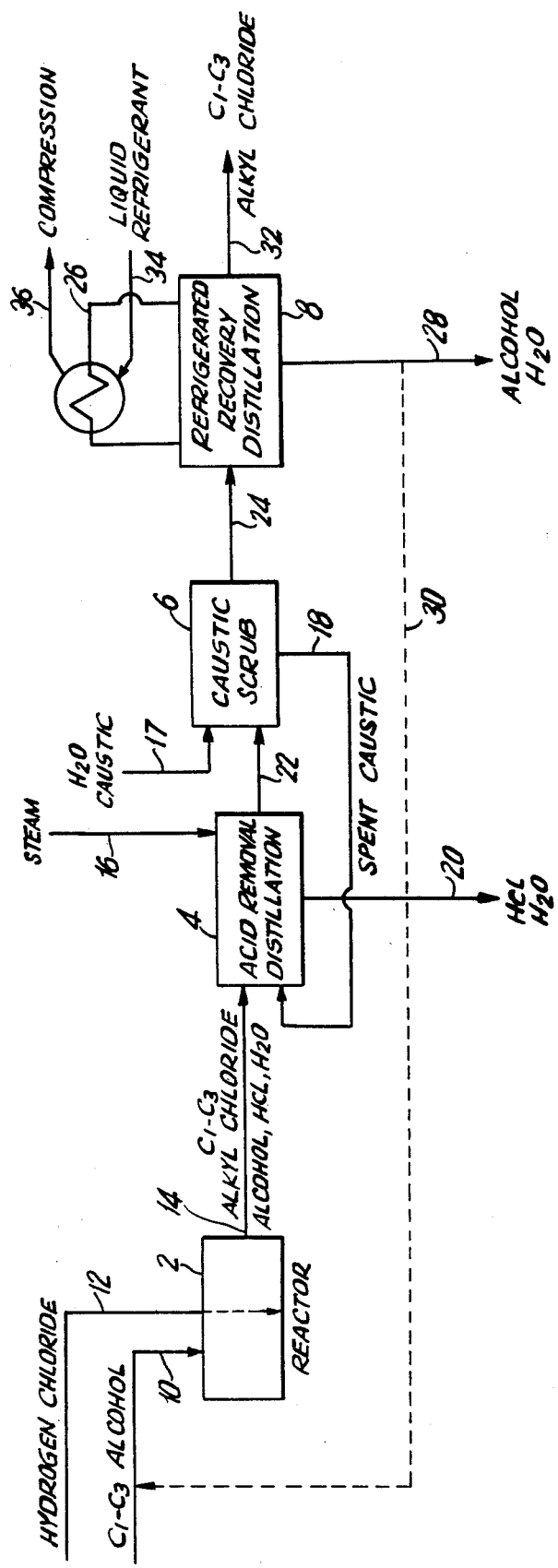
FIG. 2 shows the embodiment wherein a caustic scrub unit is interposed between the acid removal and the refrigerated units.

If the product stream contains a relatively high amount of hydrogen chloride, the caustic scrubbing embodiment as shown in FIG. 2 is used.

The first part of the process is as described in FIG. 1, but then the vapors of alkyl chloride from which the predominant amount of hydrogen chloride has been removed in said removal distillation vessel 4 are sent to scrubbing vessel 6, which can also be a column or of other suitable design, and treated with an aqueous caustic, e.g., potassium hydroxide or sodium hydroxide, solution. The concentration of caustic can vary, but preferably ranges from 3 to 25% by weight, and the temperature can also vary, but usually will be in the range of 10°-50° C. In this step, a so-called polish scrub, any remaining hydrogen chloride is converted to the corresponding alkali metal salt and water and the effluent, spent caustic solution, which also contains by-product alcohol, instead of being discharged to environmental waters, is recycled to acid removal distillation vessel 4 through conduit 18.

Next, the vapors of alkyl chloride from which substantially all of the hydrogen chloride has been removed in scrubber 6 are sent through conduit 24 to refrigerated vessel 8 and the process as described above in FIG. 1 is completed.

DESCRIPTION OF THE PREFERRED EMBODIMENTS

The following examples illustrate the process of the present invention. They are not to be construed to limit the claims in any manner whatsoever.

EXAMPLE 1

In a plant indicated generally by FIG. 1, crude methyl chloride is produced in reactor 2 by mixing methanol with hydrogen chloride in the presence of zinc chloride or other catalyst in a conventional manner, and the vapors are passed through acid removal distillation unit 4, and thereafter into refrigerated recovery distillation unit 8, and finally recovered. Methanol is charged to reactor 2 through conduit 10 and hydrogen chloride through dip tube 12. The crude gaseous product contains approximately 3-10% of unreacted methanol and about 3% of unreacted hydrogen chloride and varying amounts of water vapor, dimethyl ether and exits the reactor at a temperature of from 50° to 200° C., more usually 130°-150° C. Steam is fed to vessel 4 through conduit 16 at such a rate as to maintain the methyl chloride and other components in the vapor state and to force them upwardly and out of the vessel. Methyl chloride vapors leaving distillation vessel 4 are then sent through conduit 22 into refrigerated recovery distillation vessel 8, in which methanol is liquified by contact of the vapors with a refrigerant in loop 26. The liquified methanol is withdrawn through conduit 28 for recovery and re-use. Optionally, and preferably, the liquified alcohol product from vessel 8 can be sent through conduit 30 back to reactor 2. The methyl chloride (and some dimethyl ether) are withdrawn from distillation vessel 8 through conduit 32. The methyl chloride is recovered in a conventional fashion, e.g., by condensation or compression-liquefaction. It may be desirable for some purposes to effect a conventional removal of the final traces of waters as part of the recovery operation.

In a preferred embodiment, part of the liquified methyl chloride is used as a refrigerant for the purposes of sending it through conduit 34 into condenser loop 26, withdrawing the vaporized liquid through conduit 36 and recompressing.

EXAMPLE 2

In a plant indicated generally by FIG. 2, crude methyl chloride is produced in reactor 2 by mixing methanol with hydrogen chloride in the presence of zinc chloride or other catalyst in a conventional manner, and the vapors are passed through acid removal distillation unit 4, caustic scrubber unit 6 and refrigerated recovery distillation unit 8, and finally recovered. Methanol is charged to reactor 2 through conduit 10 and hydrogen chloride through dip tube 12. The crude gaseous product contains approximately 3-10% each of unreacted methanol and unreacted hydrogen chloride and varying amounts of water vapor, dimethyl ether and exits the reactor at a temperature of from 50° to 200° C., more usually 130°-150° C. Dilute caustic solution, e.g., 5% to 25% aqueous sodium or potassium hydroxide is fed to scrubbing vessel 6 through conduit 17 at such a rate as to maintain the volume in vessel 6, and the spent caustic is recycled through conduit 18 to vessel 4 to return the methanol to the vapor stream and keep it out of the discharged effluent. Steam is added through conduit 16, and methyl chloride vapors leaving distillation vessel 4 are passed through conduit 22 into scrubber 6 wherein they are intimately mixed with the aqueous caustic to remove the final amount of hydrogen chloride. The vapors are then sent through conduit 24 into refrigerated recovery distillation vessel 8, in which methanol is liquified by contact of the vapors with a refrigerant in loop 26. The liquified methanol is withdrawn through conduit 28 for recovery and re-use. Optionally, and preferably, the liquified alcohol product from vessel 8 can be sent through conduit 30 back to reactor 2. The methyl chloride (and some dimethyl ether) are withdrawn from distillation vessel 8 through conduit 32. The methyl chloride is recovered in a conventional fashion, e.g., by condensation or compression-liquefaction. It may be desirable for some purposes to effect a conventional removal of the final traces of water as part of the recovery operation.

In a typical procedure, the feed to the acid distillation removal column comprises about 1.0% dimethyl ether, 62% methyl chloride, 6.5% methanol, 7.3% hydrogen chloride and 23% water. Open steam is fed to the bottom of the column, the vapor into the middle and the vapor passes up. Recycle spend caustic is introduced near the middle and passes down through the column, picking up the hydrogen chloride and exiting at the bottom.

The vapor fed to the lower end of the caustic scrubber column comprises about 1.6% dimethyl ether, about 97% of methyl chloride, about 0.0006% of hydrogen chloride and about 0.012% of water. Caustic at 20% concentration and 40° C. is introduced near the top and flows down. The spent caustic material exiting and recycled to the acid distillation recovery column comprises about 58% methanol, 24.4% water, 6.7% caustic and 11% of sodium chloride.

The vapors exiting the scrubbing column are sent to the refrigerated recovery unit (the middle of a packed column in which cold liquid methyl chloride is flowing down). The fed vapors comprise about 1.3% of dimethyl ether, 84% of methyl chloride, 14% of methanol, 1.3% of water and no hydrogen chloride. The liquified condensate withdrawn from the bottom of the column comprises about 90% of methanol, 0.6% of methyl chloride and 9.4% of water. This is pure enough for recycle to the production reactor.

The product withdrawn from the top of the refrigerated alcohol recovery unit comprises about 1.6% of dimethyl ether, 98.4% of methyl chloride, nil water and nil hydrogen chloride.

In a similar fashion, ethanol, n-propanol and i-propanol are converted to ethyl chloride, n-propyl chloride and i-propyl chloride and recovered free of hydrogen chloride, alcohol and water, economically and without damage to the environment.

Although the above description has shown various modifications of the present invention, other variations are possible in the light of these teachings. It is to be understood that changes may be made in the particular embodiments of the invention described which are within the full intended scope of the appended claims.

We claim:

1. In a process for the preparation of a $C_1$-$C_3$ alkyl chloride by reacting a $C_1$-$C_3$ alcohol and hydrogen chloride in a production reactor to produce a superheated vapor of said $C_1$-$C_3$ alkyl chloride, by-product water, unreacted hydrogen chloride and unreacted $C_1$-$C_3$ alcohol, the improvement which comprises:
    (a) feeding said superheated vapor, steam and a spent aqueous caustic recycle solution to an acid removal distillation vessel to produce an acid by-product solution of the major proportion of the hydrogen chloride and removing the acid by-product solution from the vessel;
    (b) withdrawing the gaseous $C_1$-$C_3$ alkyl chloride and the gaseous unreacted $C_1$-$C_3$ alcohol from the acid removal distillation vessel and passing them into a scrubbing vessel, intimately contacting them therein with an aqueous caustic solution to remove the remaining proportion of the hydrogen chloride and to produce a spent aqueous caustic recycle solution and recycling said spent solution from the scrubbing vessel to the acid removal distillation vessel in step (a);
    (c) withdrawing the gaseous $C_1$-$C_3$ alkyl chloride and the gaseous unreacted $C_1$-$C_3$ alcohol from the scrubbing vessel and passing them into a refrigerated recovery distillation vessel wherein the unreacted $C_1$-$C_3$ alcohol is liquified and removing the liquified $C_1$-$C_3$ alcohol from the vessel; and
    (d) withdrawing and recovering the gaseous $C_1$-$C_3$ alkyl chloride from the refrigerated recovery distillation vessel.

2. A process as defined in claim 3 including the step of recycling the liquified, unreacted $C_1$-$C_3$ alcohol recovered from the refrigerated vessel in step (c) into the $C_1$-$C_3$ alkyl chloride production reactor.

3. A process as defined in claim 3 including the step of using methyl chloride as the refrigerant for the recovery distillation vessel in step (c).

4. A process as defined in claim 3 wherein the $C_1$-$C_3$ alkyl chloride is methyl chloride, ethyl chloride, n-propyl chloride or i-propyl chloride and the $C_1$-$C_3$ alcohol is, correspondingly, methanol, ethanol, n-propanol or i-propanol.

5. A process as defined in claim 3 wherein the $C_1$-$C_3$ alkyl chloride is methyl chloride and the $C_1$-$C_3$ alcohol is methanol.

6. A process as defined in claim 4 wherein the $C_1$-$C_3$ alkyl chloride is methyl chloride and the $C_1$-$C_3$ alcohol, is methanol.

7. A process as defined in claim 5 wherein the $C_1$-$C_3$ alkyl chloride is methyl chloride and the $C_1$-$C_3$ alcohol is methanol.

8. A process as defined in claim 9 wherein the methyl chloride refrigerant is a portion of the product recovered in step (d).

9. A process as defined in claim 3 wherein the caustic is sodium hydroxide or potassium hydroxide.

10. In a process for the preparation of a $C_1$-$C_3$ alkyl chloride by reacting a $C_1$-$C_3$ alcohol and hydrogen chloride to produce a superheated vapor of said $C_1$-$C_3$ alkyl chloride, by-product water, unreacted hydrogen chloride and unreacted $C_1$-$C_3$ alcohol, the improvement which comprises:

(a) distilling said superheated vapor and steam in the presence of a spent aqueous caustic solution recycled from step (b) to produce an acid by-product solution, said acid by-product solution comprising a major proportion of the hydrogen chloride, and removing the acid by-product solution;

(b) contacting the remaining gaseous $C_1$-$C_3$ alkyl chloride and the gaseous unreacted $C_1$-$C_3$ alcohol from step (a) with an aqueous caustic solution to remove the remaining proportion of the hydrogen chloride and to produce a spent aqueous caustic solution and recycling said spent aqueous caustic solution for use in step (a);

(c) subjecting the remaining gaseous $C_1$-$C_3$ alkyl chloride and the gaseous unreacted $C_1$-$C_3$ alcohol from step (b) to refrigerated recovery distillation wherein the unreacted $C_1$-$C_3$ alcohol is liquified and removing the resultant liquified $C_1$-$C_3$ alcohol; and (d) recovering the remaining gaseous $C_1$-$C_3$ alkyl chloride.

11. A process as defined in claim 10 including the step of recycling the liquified, unreacted $C_1$-$C_3$ alcohol recovered from step (c) for use in the initial reaction of the $C_1$-$C_3$ alcohol with hydrochloric acid.

12. A process as defined in claim 10 including the step of using methyl chloride as the refrigerant for the recovery distillation in step (c).

13. A process as defined in claim 10 wherein the $C_1$-$C_3$ alkyl chloride is methyl chloride, ethyl chloride, n-propyl chloride or i-propyl chloride and the $C_1$-$C_3$ alcohol is, correspondingly, methanol, ethanol, n-propanol or i-propanol.

14. A process as defined in claim 10 wherein the $C_1$-$C_3$ alkyl chloride is methyl chloride and the $C_1$-$C_3$ alcohol is methanol.

15. A process as defined in claim 11 wherein the $C_1$-$C_3$ alkyl chloride is methyl chloride and the $C_1$-$C_3$ alcohol, is methanol.

16. A process as defined in claim 12 wherein the $C_1$-$C_3$ alkyl chloride is methyl chloride and the $C_1$-$C_3$ alcohol is methanol.

17. A process as defined in claim 16 wherein the methyl chloride refrigerant is a portion of the product recovered in step (d).

18. A process as defined in claim 10 wherein the caustic is sodium hydroxide or potassium hydroxide.

* * * * *

UNITED STATES PATENT AND TRADEMARK OFFICE
CERTIFICATE OF CORRECTION

PATENT NO. : 4,220,609
DATED : September 2, 1980
INVENTOR(S) : Harry R. McEntee et al It is certified that error appears in the above-identified patent and that said Letters Patent are hereby corrected as shown below:

In Col. 6, line 60, "3" should read -- 1 --; at line 64, "3", second occurrence, should read -- 1 --; at line 67, "3" should read -- 1 --.

In Col. 7, line 4, "3" should read -- 1 --; at line 7, "4" should read -- 2 --; at line 10, "5" should read -- 3 --; at line 13, "9" should read -- 7 --; at line 16, "3" should read -- 1 --.

Signed and Sealed this

Twenty-seventh Day of January 1981

[SEAL]

Attest:

RENE D. TEGTMEYER

Attesting Officer

Acting Commissioner of Patents and Trademarks